United States Patent [19]

Ehrenfreund

[11] 4,262,020
[45] * Apr. 14, 1981

[54] ACYLUREA INSECTICIDES

[75] Inventor: Josef Ehrenfreund, Allschwil, Switzerland

[73] Assignee: Ciba-Geigy Corporation, Ardsley, N.Y.

[*] Notice: The portion of the term of this patent subsequent to Jul. 24, 1996, has been disclaimed.

[21] Appl. No.: 16,867

[22] Filed: Mar. 2, 1979

[30] Foreign Application Priority Data

Mar. 13, 1978 [CH] Switzerland .......................... 2700/78
Jan. 30, 1979 [CH] Switzerland ............................ 884/79

[51] Int. Cl.³ ....................... C07C 127/22; A01N 9/20
[52] U.S. Cl. ....................................... 424/322; 564/44
[58] Field of Search ..................... 260/553 E; 424/322

[56] References Cited

U.S. PATENT DOCUMENTS

| | | | |
|---|---|---|---|
| 4,013,717 | 3/1977 | Wellinga et al. | 260/553 E |
| 4,089,975 | 5/1978 | Wade et al. | 260/553 E X |
| 4,162,330 | 7/1979 | Ehrenfreund | 260/553 E X |
| 4,170,657 | 10/1979 | Rigterink | 424/322 |

FOREIGN PATENT DOCUMENTS 2601780 7/1977 Fed. Rep. of Germany ....... 260/553 E
2820696 11/1978 Fed. Rep. of Germany .

Primary Examiner—Thomas A. Waltz
Attorney, Agent, or Firm—Frederick H. Rabin

[57] ABSTRACT

New substituted N-phenyl-N'-fluorobenzoylureas of the formula

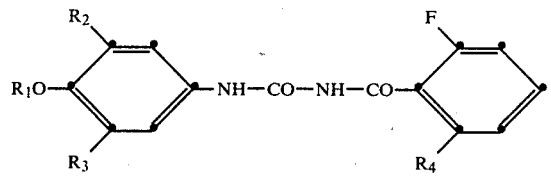

wherein $R_1$ is a $C_2$-$C_3$-alkenyl group, a $C_2$-$C_4$-alkenyl group mono- or disubstituted by chlorine, or it is the propargyl group, $R_2$ and $R_3$ independently of one another are hydrogen or chlorine, and $R_4$ is hydrogen or fluorine; processes for producing the said compounds and their use for combating pests, especially for the control of insects and representatives of the order Acarina, which infest plants and animals. The new compounds also have an antifeedant action on insects which cause damage to plants.

25 Claims, No Drawings

ACYLUREA INSECTICIDES

The present invention relates to novel substituted N-phenyl-N'-fluorobenzoylureas, to processes for producing them, and to their use for combating pests.

The substituted N-phenyl-N'-fluorobenzoylureas according to the invention have the formula I

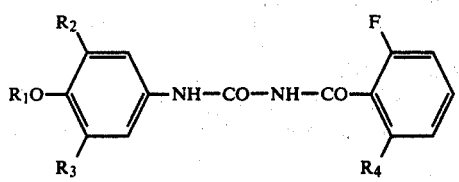

in which $R_1$ is a $C_2$–$C_3$-alkenyl group, a $C_2$–$C_4$-alkenyl group mono- or disubstituted by chlorine, or it is the propargyl group, $R_2$ and $R_3$ independently of one another are hydrogen or chlorine, and $R_4$ is hydrogen or fluorine.

Compounds of the formula I which are preferred by virtue of their action as pesticidal agents are those in which $R_2$ and $R_3$ are each chlorine. To be emphasised apart from these compounds are compounds of the formula I in which $R_1$ is a $C_2$–$C_4$-alkenyl group monosubstituted by chlorine, especially the radical $Cl-CH=CH-CH_2-$.

Valuable compounds on account of their biological effectiveness are moreover the compounds of the formula I in which $R_1$ is the radical

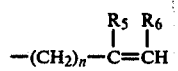

in which $R_5$ and $R_6$ independently of one another are hydrogen or chlorine.

Of particular interest also are compounds of the formula I in which $R_2$ and $R_3$ are hydrogen. Compounds of the formula I according to the invention which are especially effective are those in which $R_4$ is fluorine.

The compounds of the formula I are obtained—where this is at all possible—as cis/trans isomeric mixtures. In this respect, the term 'compounds of the formula I' is to be understood as embracing both the cis and trans forms and the corresponding isomeric mixtures. An isomeric mixture can be separated, for example, by means of the known chromatographical methods of separation and subsequent elution into the isomeric forms. For the synthesis of stereochemically homogeneous compounds of the formula I, there are advantageously used stereochemically homogeneous starting compounds of the following formula II or IV.

The compounds of the formula I can be produced by processes known per se (see, inter alia, the German Offenlegungsschriften Nos. 2,123,236 and 2,601,780).

Thus, for example, a compound of the formula I can be obtained by reaction (a) of a compound of the formula II

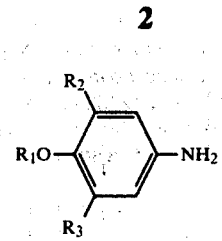

with a compound of the formula III

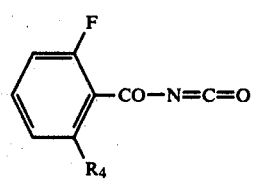

or (b) of a compound of the formula IV

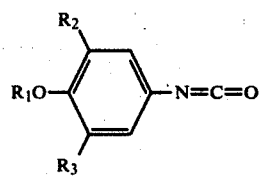

with a compound of the formula V

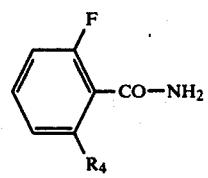

In the above formulae II, III, IV and V, the radicals $R_1$, $R_2$, $R_3$ and $R_4$ have the meanings given under the formula I.

The processes (a) and (b) mentioned can be preferably performed under normal pressure and in the presence of an organic solvent or diluent. Suitable solvents or diluents are for example: ethers and ethereal compounds such as diethyl ether, dipropyl ether, dibutyl ether, dioxane, dimethoxyethane and tetrahydrofuran; N,N-dialkylated carboxylic acid amides; aliphatic, aromatic and also halogenated hydrocarbons, particularly benzene, toluene, xylene, chloroform, methylene chloride, carbon tetrachloride and chlorobenzene; nitriles such as acetonitrile or propionitrile; dimethylsulfoxide, as well as ketones, for example acetone, methyl ethyl ketone, methylisopropyl ketone and methylisobutyl ketone. Process (a) is in general performed at a temperature of $-10°$ to $100°$ C., preferably between $15°$ and $25°$ C., optionally in the presence of an organic base, for example triethylamine. The process (b) is performed at a temperature of $0°$ to $120°$ C., preferably at the boiling point of the employed solvent, and optionally in the presence of an organic base, such as pyridine, and/or with the addition of an alkali salt or alkaline-earth metal salt, preferably sodium.

The starting materials of the formulae II, III, IV and V are known, or can be produced by processes analogous to known processes.

It is already known that specific N-phenyl-N'-benzoylureas have insecticidal properties (see German Offenlegungschriften Nos. 2,123,236, 2,504,982, 2,537,413 and 2,601,780, the Belgian Pat. Nos. 832,304, 843,906, 844,066 and 867,046, and also the U.S. Pat. No. 4,089,975).

It has now been found that, surprisingly, the N-phenyl-N'-fluorobenzoylureas of the formula I of the invention, whilst having good tolerance to plants and negligible toxicity to warm-blooded animals, are excellently effective as pesticidal agents. They are suitable in particular for combating pests which infest plants and animals.

The compounds of the formula I are especially suitable for combating insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae; as well as for combating acarids of the families: Ixodidae, Argasidae, Tetranychidae and Dermanyssidae.

In addition to having a favourable action against flies, such as *Musca domestica*, and mosquitoes, the compounds of the formula I are suitable also for the control of insects which damage plants by eating, in crops of ornamental plants and useful plants, especially in cotton crops (for example against *Spodoptera littoralis* and *Heliothis virescens*) and in crops of vegetables (for example against *Leptinotarsa decemlineata* and *Pieris brassicae*). The ovicidal and ovolarvicidal action of compounds of the formula I is also to be emphasised.

The compounds of the formula I are moreover suitable for combating ectoparasites in domestic animals and productive animals, for example by the treatment of animals, livestock housing or pasture land.

The action of the compounds of the invention or of compositions containing them can be substantially broadened and adapted to suit given circumstances by the addition of other insecticides and/or acaricides. Suitable as additives are for example the following active substances:
organic phosphorus compounds,
nitrophenols and derivatives,
formamidines, ureas,
carbamates and
chlorinated hydrocarbons.

The compounds of the formula I can be combined with particular advantage also with substances which have a pesticidally intensifying effect. Examples of such compounds are, inter alia: piperonylbutoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioates.

The compounds of the formula I can be used on their own or together with suitable carriers and/or additives. Suitable carriers and additives may be solid or liquid and correspond to the substances common in formulation practice, such as natural or regenerated substances, solvents, dispersing agents, wetting agents, adhesives, thickeners, binders and/or fertilisers. For application, the compounds of the formula I can be processed into the form of dusts, emulsion concentrates, granulates, dispersions, sprays, solutions or suspensions, the formulation of these preparations being effected in a manner commonly known in the art. Also to be mentioned are cattle dips and spray races, in which aqueous preparations are used. These forms of preparation are particularly suitable for combating zooparasitic pests.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:

solid preparations:
  dusts, scattering agents or granulates (coated granules, impregnated granules and homogeneous granules);
liquid preparations:
  (a) water-dispersible concentrates of active substance: wettable powders, pastes or emulsions;
  (b) solutions.

The content of active substance in the described compositions is between 0.1 and 95%.

The active substances of the formula I can be formulated for example as follows:

Dusts

The following substances are used to produce (a) a 5% dust and (b) a 2% dust:

(a)

5 parts of active substance, and
95 parts of talcum;

(b)

2 parts of active substance,
1 part of highly dispersed silicic acid, and
97 parts of talcum.

The active substance is mixed and ground with the carriers.

Granulate

The following ingredients are used to produce a 5% granulate:
5 parts of active substance,
0.25 part of epichlorohydrin,
0.25 part of cetyl polyglycol ether,
3.50 parts of polyethylene glycol, and
91 parts of kaolin (particle size 0.3–0.8 mm).

The active substance is mixed with epichlorohydrin and dissolved in 6 parts of acetone, and the polyethylene glycol and cetyl polyglycol ether are then added. The solution obtained is sprayed onto kaolin and the acetone is subsequently evaporated off.

Wettable powders

The following constituents are used to produce (a) a 40% wettable powder, (b) and (c) a 25% wettable powder, and (d) a 10% wettable powder:

(a)

40 parts of active substance,
5 parts of sodium lignin sulfonate,
1 part of sodium dibutyl-naphthalene sulfonate, and
54 parts of silicic acid;

(b) 25 parts of active substance, 4.5 parts of calcium lignin sulfonate,
1.9 parts of Champagne chalk/hydroxyethyl cellulose mixture (1:1),
1.5 parts of sodium dibutyl-naphthalene sulfonate,
19.5 parts of silicic acid, 19.5 parts of Champagne chalk, and
28.1 parts of kaolin;

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminum silicate,
16.5 parts of kieselgur, and
46 parts of kaolin;

(d) 10 parts of active substance,
3 parts of a mixture of the sodium salts of saturated fatty alcohol sulfates,
5 parts of naphthalenesulfonic acid/formaldehyde condensate, and
82 parts of kaolin.

The active substance is intimately mixed in suitable mixers with the additives, and the mixture is then ground in the appropriate mills and rollers to obtain wettable powders which can be diluted with water to give suspensions of the desired concentration.

Emulsifiable concentrates

The following substances are used to produce (a) a 10% emulsifiable concentrate, (b) a 25% emulsifiable concentrate and (c) a 50% emulsifiable concentrate:

(a) 10 parts of active substance,
3.4 parts of epoxidised vegetable oil,
3.4 parts of a combination emulsifier consisting of fatty alcohol polyglycol ether and alkylaryl sulfonate calcium salt,
40 parts of dimethylformamide, and
43.2 parts of xylene;

(b)

25 parts of active substance,
2.5 parts of epoxidised vegetable oil,
10 parts of an alkylarylsulfonate/fatty alcohol polyglycol ether mixture,
5 parts of dimethylformamide, and
57.5 parts of xylene;

(c)

50 parts of active substance,
4.2 parts of tributylphenol-polyglycol ether,
5.8 parts of calcium-dodecylbenzenesulfonate,
20 parts of cyclehexanone, and
20 parts of xylene.

Emulsions of the concentration required can be prepared from these concentrates by dilution with water.

Spray

The following constituents are used to produce (a) a 5% spray and (b) a 95% spray:

(a)

5 parts of active substance,
1 part of epichlorohydrin, and
94 parts of ligroin (boiling limits 160°–190° C.);

(b) 95 parts of active substance, and
5 parts of epichlorohydrin.

The invention is further illustrated by the following Examples.

EXAMPLE 1

3 g of 2,6-difluorobenzoylisocyanate, dissolved in 10 ml of absolute ether is added dropwise at room temperature to a solution of 3.3 g of N-3,5-dichloro-4-(3'-chloroallyloxy)-aniline in 30 ml of absolute ether. The precipitate separating out after a short time is filtered off under suction and washed with ether. Recrystallisation from ethyl acetate yields analytically pure N-3,5-dichloro-4-(3'-chloroallyloxy)-phenyl-N'-difluorobenzoylurea having a melting point of 135°–137° C. (as a mixture of stereoisomers).

EXAMPLE 2

A mixture of 5.0 g of N-3,5-dichloro-4-allyloxyphenylisocyanate, 3.5 g of 2,6-difluorobenzamide, 0.5 g of sodium and 25 ml of pyridine is heated at 100° C. for 24 hours. The reaction mixture is then poured onto ice, and the solid substance which has precipitated is washed with water and alcohol. The precipitate is subsequently recrystallised from acetonitrile to thus obtain N-3,5-dichloro-4-allyloxyphenyl-N'-2,6-difluorobenzoylurea having a melting point of 161°–163° C.

The following compounds of the formula I are produced by methods analogous to those described in the preceding Examples:

| $R_1$ | $R_2$ | $R_3$ | $R_4$ | Melting point [°C.] |
|---|---|---|---|---|
| $CH_2=CCl-CH_2-$ | Cl | Cl | F | 172–174 |
| $Cl_2C=CH-CH_2-$ | Cl | Cl | F | 176–178 |
| $HC\equiv C-CH_2-$ | Cl | Cl | F | 226–227 |
| $ClCH=CCl-$ | Cl | Cl | F | 190–192 |
| $ClCH=CCl-CH_2-$ | Cl | Cl | F | 188–193(*) |
| $ClCH=CH-CH_2-$ | H | H | F | 162–180(*) |
| $ClCH=CCl-$ | H | H | F | 178–179(*) |
| $CH_2=CH-CH_2-$ | Cl | Cl | H | 165–166 |
| $CH_2=CCl-CH_2-$ | Cl | Cl | H | 190–192 |
| $ClCH=CH-CH_2-$ | Cl | Cl | H | 177–178(*) |
| $ClCH=CCl-$ | Cl | Cl | H | 171–172 |
| $Cl_2C=CH-CH_2-$ | Cl | H | F |  |
| $ClCH=CH-CH_2-$ | Cl | H | F | 164–186(*) |
| $CH_2=CCl-CH_2-$ | Cl | H | F | 180–181 |
| $CH_2=CH-CH_2$ | Cl | H | H | 182–184 |
| $CH_2=CH-CH_2-$ | Cl | H | F | 182–184 |
| $CH_2=CH-CH_2-$ | H | H | F | 174–176 |
| $ClCH=CH-CH_2$ | Cl | H | H | 143–147(*) |
| $CH_3-CCl=CH-CH_2$ | Cl | Cl | F | 156–158 |
| $CH_3-CCl=CH-CH_2$ | H | H | F | 187–188 |
| $CH_2=CCl-CH_2$ | Cl | H | H | 159–160 |
| $ClCH=CCl-CH_2-$ | Cl | H | H | (*) |
| $ClCH=CCl-CH_2-$ | Cl | H | F | (*) |
| $Cl_2C=CH-CH_2-$ | Cl | H | H |  |
| $Cl_2C=CH-$ | Cl | H | H |  |
| $Cl_2C=CH-$ | Cl | H | F |  |
| $Cl_2C=CH-$ | H | H | H |  |
| $Cl_2C=CH-$ | H | H | F |  |
| $ClCH=CCl-$ | Cl | H | F | 197–203 |
| $ClCH=CCl-$ | Cl | H | H | 182–183 |
| $CH_3-CCl=CH-CH_2-$ | Cl | Cl | H | 182–183(*) |

(*)mixture of stereoisomers

EXAMPLE 3

1.85 g of 2,6-difluorobenzoylisocyanate, dissolved in 10 ml of absolute ether, is added dropwise, at room temperature, to a solution of 2.5 g of 3,5-dichloro-4-(3'-trans-chloroallyloxy)-aniline in 30 ml of absolute ether. The precipitate separating out after a short time is filtered off under suction and washed with ether. Recrystallisation from toluene yields isomerically pure N-3,5-dichloro-4-(3'-trans-chloroallyloxy)-phenyl-N'-2,6- difluorobenzoylurea having a melting point of 175.5°-177.5° C.

The following compounds are obtained in an analogous manner, that is to say, starting with the appropriate stereochemically homogeneous anilines:

| $R_1$ | $R_2$ | $R_3$ | $R_4$ | Melting point [°C.] |
|---|---|---|---|---|
| $ClCH{=}CH{-}CH_2{-}$ | Cl | Cl | F | 145–146.5 (cis isomer) |
| $ClCH{=}CH{-}CH_2{-}$ | H | H | F | 196–198 (trans isomer) |
| $ClCH{=}CH{-}CH_2{-}$ | H | H | F | 170–172 (cis isomer) |

EXAMPLE 4

Action against *Musca domestica*

50 g amounts of freshly prepared CSMA nutrient medium for maggots was weighed off into each of a series of beakers. A specific amount of a 1% (by weight) acetonic solution of the respective active substance was transferred by pipette to the nutrient medium in each beaker. After a thorough mixing of the nutrient medium, the acetone was allowed to evaporate off for at least 20 hours. There were then deposited per active substance and concentration in each case 25 one-day-old *Musca domestica* maggots into each beaker containing the treated nutrient medium. After completion of pupation, the formed pupae were separated from the nutrient medium by flushing with water, and were placed into vessels closed with perforated lids. The pupae flushed out per batch were counted (toxic effect of the active substance on the development of the maggot), and then after 10 days the number of flies which had emerged from the pupae was determined.

Compounds according to the Examples 1 to 3 exhibited a good action in the above test.

EXAMPLE 5

Action against *Lucilia sericata*

1 ml of an aqueous solution containing 0.5% of active substance was added to 9 ml of a culture medium at 50° C. About 30 freshly emerged *Lucilia sericata* maggots were then placed onto the culture medium, and after 48 and 96 hours, respectively, the insecticidal action was determined by ascertaining the mortality rate.

Compounds according to the Examples 1 to 3 exhibited in this test a good action against *Lucilia sericata*.

EXAMPLE 6

Action against *Aedes aegypti*

Sufficient of a 0.1% acetonic solution of the respective active substance was transferred by pipette to the surface of 150 ml of water in a container to obtain concentrations of 10, 5 and 1 ppm in each case. After the acetone had evaporated off, 30–40 two-day-old Aëdes larvae were placed into each container. The mortality rate was ascertained after 1, 2 and 5 days.

Compounds according to Examples 1 to 3 exhibited in this test a good action against *Aedes aegypti*.

EXAMPLE 7

Insecticidal stomach poison action

Cotton plants were sprayed with a 0.05% aqueous emulsion of the active substance (obtained from a 10% emulsifiable concentrate).

After drying of the resulting coating, Spodoptera littoralis larvae and Heliothis virescens larvae in the third larval stage were placed onto the cotton plants. The test was carried out at 24° C. with 60% relative humidity.

Compounds according to the Examples 1 to 3 exhibited in the above test a good insecticidal stomach poison action against the larvae of Spodoptera littoralis and Heliothis virescens.

EXAMPLE 8

Ovicidal action on *Spodoptera littoralis*

Eggs of *Spodoptera littoralis*, deposited on filter paper, were cut out of the paper and immersed in a 0.05% (by weight) solution of the active substance in a acetone/water mixture (1:1). The deposited eggs treated in this manner were then taken out of the mixture, and placed at 21° C. with 60% relative humidity into plastic dishes. After 3 to 4 days, the hatching rate, that is to say, the number of larvae which had developed from the treated eggs, was determined.

The compounds according to the invention which are given in Examples 1–3 exhibited a good action in the above test.

What is claimed is:

1. A compound of the formula I $$R_1O-\underset{R_3}{\overset{R_2}{\bigcirc}}-NH-CO-NH-CO-\underset{R_4}{\overset{F}{\bigcirc}} \quad (I)$$

in which $R_1$ is a $C_2$–$C_3$-alkenyl group, a $C_2$–$C_4$-alkenyl group mono- or distributed by chlorine, or it is the propargyl group, $R_2$ and $R_3$ independently of one another are hydrogen or chlorine, and $R_4$ is hydrogen or fluorine.

2. A compound of the formula I according to claim 1 wherein $R_2$ and $R_3$ are each chlorine.

3. A compound of the formula I according to claim 1 or 2, wherein $R_1$ is a $C_2$–$C_4$-alkenyl group which is monosubstituted by chlorine.

4. A compound of the formula I according to claim 3 wherein $R_1$ is the radical $Cl-CH{=}CH-CH_2-$.

5. A compound of the formula I according to claim 1 or 2, wherein $R_1$ is the radical $$-(CH_2)_n-\underset{|}{\overset{R_5}{C}}{=}\underset{|}{\overset{R_6}{C}}H$$

in which $R_5$ and $R_6$ independently of one another are each hydrogen or chlorine, and n is naught or 1.

6. A compound of the formula I according to claim 1 or 2 wherein $R_2$ and $R_3$ are each hydrogen.

7. A compound of the formula I according to claims 1 or 2, wherein R₄ is fluorine.

8. The compound according to claim 7 of the formula

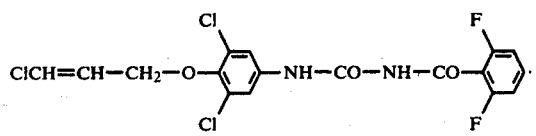

9. The compound according to claim 7 of the formula

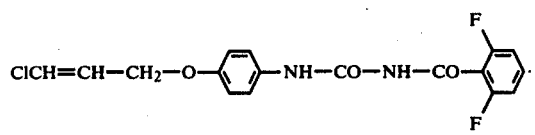

10. The compound according to claim 7 of the formula

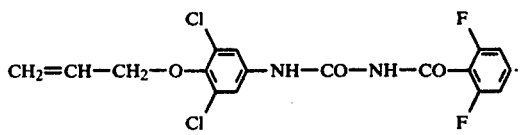

11. The compound according to claim 2 of the formula

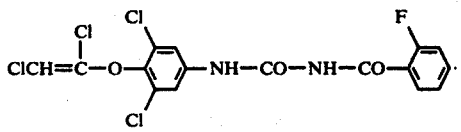

12. The compound according to claim 2 of the formula

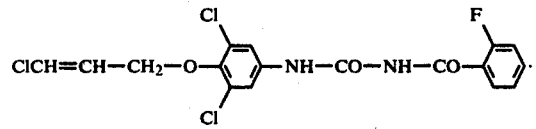

13. An insecticidal and acaracidal composition containing an insecticidally or acaricidally effective amount of a compound according to claim 1 as active ingredient, together with suitable carriers.

14. A method of combatting insects and acarids which comprises applying thereto an insecticidally or acaricidally effective amount of a compound according to claim 1.

15. A method of combatting insects and acarids which comprises applying thereto an insecticidally or acaricidally effective amount of a compound according to claim 2.

16. A method of combatting insects and acarids which comprises applying thereto an insecticidally or acaricidally effective amount of a compound according to claim 3.

17. A method of combatting insects and acarids which comprises applying thereto an insecticidally or acaricidally effective amount of a compound according to claim 4.

18. A method of combatting insects and acarids which comprises applying thereto an insecticidally or acaricidally effective amount of a compound according to claim 5.

19. A method of combatting insects and acarids which comprises applying thereto an insecticidally or acaricidally effective amount of a compound according to claim 6.

20. A method of combatting insects and acarids which comprises applying thereto an insecticidally or acaricidally effective amount of a compound according to claim 7.

21. A method of combatting insects and acarids which comprises applying thereto an insecticidally or acaricidally effective amount of the compound of claim 8.

22. A method of combatting insects and acarids which comprises applying thereto an insecticidally or acaricidally effective amount of the compound of claim 9.

23. A method of combatting insects and acarids which comprises applying thereto an insecticidally or acaracidally effective amount of the compound of claim 10.

24. A method of combatting insects and acarids which comprises applying thereto an insecticidally or acaricidally effective amount of the compound of claim 11.

25. A method of combatting insects and acarids which comprises applying thereto an insecticidally or acaricidally effective amount of the compound of claim 12.

* * * * *